(12) United States Patent  (10) Patent No.: US 7,060,048 B1
Nat et al.  (45) Date of Patent: Jun. 13, 2006

(54) NEEDLELESS SYRINGE

(75) Inventors: Avtar S. Nat, Fremont, CA (US);
Stuart P. Hendry, Oxford (GB); Colin Sheldrake, Oxford (GB)

(73) Assignee: PowerJect Research Limited, Oxford (GB)

( * ) Notice: Subject to any disclaimer, the term of this patent is extended or adjusted under 35 U.S.C. 154(b) by 0 days.

(21) Appl. No.: 09/548,984

(22) Filed: Apr. 14, 2000

Related U.S. Application Data

(60) Provisional application No. 60/129,657, filed on Apr. 16, 1999.

(51) Int. Cl.
*A61M 5/30* (2006.01)

(52) U.S. Cl. .......................................... 604/70; 604/49
(58) Field of Classification Search ................ 604/68, 604/70, 232, 414, 49, 131, 141
See application file for complete search history.

(56) References Cited

U.S. PATENT DOCUMENTS

| 2,645,223 A | | 7/1953 | Lawshe et al. | |
|---|---|---|---|---|
| 4,945,050 A | | 7/1990 | Sanford et al. | |
| 5,026,343 A | * | 6/1991 | Holzer ........................ | 604/68 |
| 5,036,006 A | | 7/1991 | Sanford et al. | |
| 5,120,657 A | | 6/1992 | McCabe et al. | |
| 5,149,655 A | | 9/1992 | McCabe et al. | |
| 5,179,022 A | | 1/1993 | Sanford et al. | |
| 5,371,015 A | | 12/1994 | Sanford et al. | |
| 5,383,851 A | * | 1/1995 | McKinnon et al. ........... | 604/68 |
| 5,405,779 A | | 4/1995 | McCabe et al. | |
| 5,478,744 A | | 12/1995 | Sanford et al. | |
| 5,506,125 A | | 4/1996 | McCabe et al. | |
| 5,525,510 A | | 6/1996 | McCabe et al. | |
| 5,630,796 A | * | 5/1997 | Bellhouse et al. ............ | 604/49 |
| 5,851,198 A | * | 12/1998 | Castellano et al. ........... | 604/68 |
| 5,865,798 A | | 2/1999 | Grimard et al. | |
| 5,899,880 A | * | 5/1999 | Bellhouse et al. ............ | 604/70 |
| 5,919,159 A | * | 7/1999 | Lilley et al. .................. | 604/70 |
| 5,993,412 A | * | 11/1999 | Deily et al. ................... | 604/68 |
| 6,004,286 A | | 12/1999 | Bellhouse et al. | |
| 6,013,050 A | * | 1/2000 | Bellhouse et al. ............ | 604/70 |
| 6,132,395 A | * | 10/2000 | Landau et al. ................ | 604/68 |
| 6,174,304 B1 | * | 1/2001 | Weston ........................ | 604/414 |
| 6,210,359 B1 | * | 4/2001 | Patel et al. .................... | 604/68 |
| 6,258,062 B1 | * | 7/2001 | Thielen et al. ............... | 604/141 |
| 6,309,371 B1 | * | 10/2001 | Dedoer et al. ................ | 604/68 |
| 6,328,714 B1 | * | 12/2001 | Bellhouse et al. .......... | 604/232 |
| 2001/0027293 A1 | * | 10/2001 | Joshi ........................... | 604/131 |

* cited by examiner

*Primary Examiner*—Manuel Mendez
(74) *Attorney, Agent, or Firm*—Foley & Lardner LLP

(57) ABSTRACT

A needleless syringe device for accelerating particles into a target tissue of a vertebrate subject is provided. The syringe features an elongate, tubular duct having a lumen for delivering the particles towards the target tissue. The duct may have a constant cross-sectional area. The device further features a receptacle holding the particles and a gas discharge chamber upstream of the receptacle. On actuation the gas discharge chamber discharges pressurised gas having a maximum total pressure of about 10 bar or less. Methods of using the device for delivering particles to a target tissue are also provided.

43 Claims, 7 Drawing Sheets

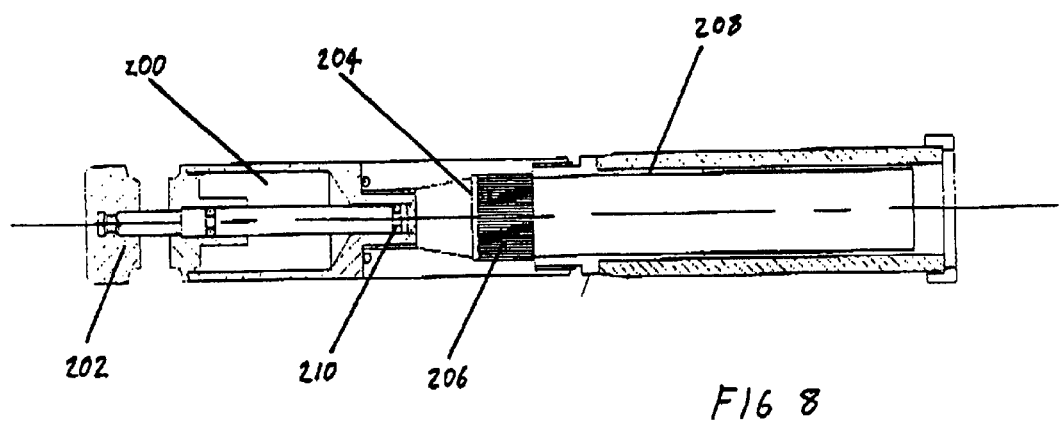
FIG 8
FIG 11
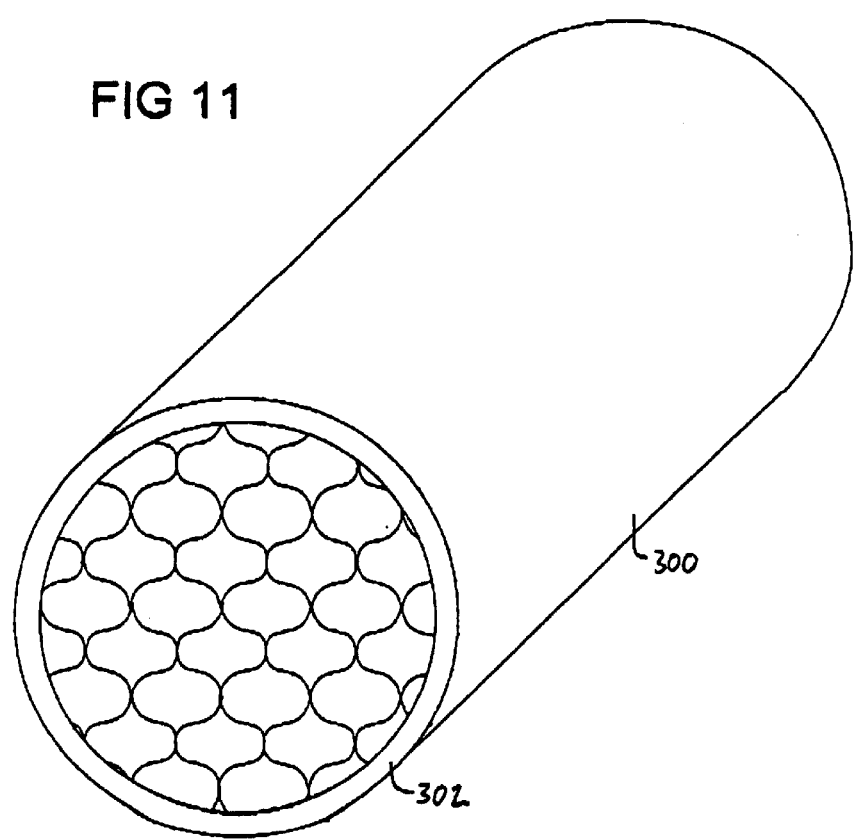

NEEDLELESS SYRINGE

This application claims the benefit of provisional application Ser. No. 60/129,657 filed Apr. 6, 1999.

TECHNICAL FIELD

The present invention relates generally to a needleless syringe device for accelerating particles for delivery into target tissue of a vertebrate subject.

BACKGROUND

The ability to deliver pharmaceuticals through skin surfaces (transdermal delivery) provides many advantages over oral or parenteral delivery techniques. In particular, transdermal delivery provides a safe, convenient and noninvasive alternative to traditional drug administration systems, conveniently avoiding the major problems associated with oral delivery (e.g. variable rates of absorption and metabolism, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles). In addition, transdermal delivery affords a high degree of control over blood concentrations of administered pharmaceuticals.

Recently, a novel transdermal drug delivery system that entails the use of a needleless syringe to fire powders (i.e. solid drug-containing particles) in controlled doses into and through intact skin has been described. In particular, U.S. Pat. No. 5,630,796 to Bellhouse et al. describes a needleless syringe that delivers pharmaceutical particles entrained in a supersonic gas flow. The needleless syringe is used for transdermal delivery of powdered drug compounds and compositions, for delivery of genetic material into living cells (e.g. gene therapy) and for the delivery of biopharmaceuticals to skin, muscle, blood or lymph. The needleless syringe can also be used in conjunction with surgery to deliver drugs and biologics to organ surfaces, solid tumors and/or to surgical cavities (e.g. tumor beds or cavities after tumor resection). In theory, practically any pharmaceutical agent that can be prepared in a substantially solid, particulate form can be safely and easily delivered using such devices.

One needleless syringe described in Bellhouse et al. comprises an elongate tubular converging-diverging nozzle having a rupturable membrane initially closing the passage through the nozzle and arranged substantially adjacent to the upstream end of the nozzle. Particles of a therapeutic agent to be delivered are disposed adjacent to the rupturable membrane and are delivered using an energizing means which applies a gaseous pressure to the upstream side of the membrane sufficient to burst the membrane and produce a supersonic gas flow (containing the pharmaceutical particles) through the nozzle for delivery from the downstream end thereof. The particles can thus be delivered from the needleless syringe at delivery velocities of between Mach 1 and Mach 8 which are readily obtainable upon the bursting of the rupturable membrane. The passage through the nozzle has an upstream convergent portion, leading through a throat to a downstream, divergent portion. The converging-diverging passage is used to accelerate the gas to supersonic speed. The gas is first brought to Mach 1 in the throat and the downstream divergence accelerates it to a steady state supersonic speed.

Transdermal delivery using the needleless syringe described in Bellhouse et al. is carried out with particles having an approximate size that generally ranges between 0.1 and 250 µm. For drug delivery, an optimal particle size is usually at least about 10 to 15 µm (the size of a typical cell). For gene delivery, an optimal particle size is generally substantially smaller than 10 µm. Particles larger than about 250 µm can also be delivered from the device, with the upper limitation being the point at which the size of the particles would cause untoward damage to the skin cells. The actual distance which the delivered particles will penetrate depends upon particle size (e.g. the nominal particle diameter assuming a roughly spherical particle geometry), particle density, the initial velocity at which the particle impacts the skin surface, and the density and kinematic viscosity of the skin. In this regard, optimal particle densities for use in needleless injection generally range between about 0.1 and 25 $g/cm^3$, preferably between about 0.8 and 1.5 $g/cm^3$, and injection velocities generally range between about 100 and 3000 m/sec. These particle size and density ranges are also appropriate to the present invention, although larger and/or more dense particles can be used in the present invention due to the particle-skin impact speed generally being significantly less, for example as low as 50 m/s.

SUMMARY OF THE INVENTION

According to a first aspect of the present invention there is provided a needleless syringe device for accelerating particles into a target tissue of a vertebrate subject, said syringe comprising:

an elongate, tubular duct having a lumen for delivering the particles towards the target tissue, the duct having an upstream end and a downstream end;

a receptacle holding the particles to be accelerated; and a gas discharge chamber, upstream of the receptacle, for the controlled discharge therefrom of pressurized gas to accelerate the particles from the receptacle down the duct lumen towards the target tissue;

wherein the pressurised gas discharged from the gas discharge chamber has a maximum total pressure of about 10 bar or less.

In one embodiment the gas discharge chamber comprises a cylinder containing a piston movable therein between first and second positions. To effect a said controlled gas discharge the piston is driven by a spring along the cylinder from its first position to its second position. A priming arrangement is provided to enable the piston to be drawn back from its second position to its first position to compress the spring and thus to prime the gas delivery chamber. An actuation trigger is provided for releasing the piston from its first position once the gas delivery chamber is primed.

In a further embodiment of the invention the gas delivery chamber comprises a canister pre-charged with gas. This gas may, for example, be $CO_2$, He, N or air.

In both preferred embodiments of the device the duct lumen does not necessarily converge and then diverge to form a throat.

According to a second aspect of the present invention there is provided a disposable duct/receptacle assembly for use in a device having the construction recited above in the first aspect of the present invention, wherein the assembly comprises a said duct integral with a said particle-containing receptacle and the assembly is disconnectable from the gas discharge chamber whereby, after a said controlled gas discharge has been effected to accelerate the particles from the receptacle and the duct, the assembly can be separated from the gas discharge chamber and replaced in the device with a fresh disposable assembly.

According to a third aspect of the present invention there is provided a method of discharging particles from a needleless syringe suitable for accelerating the particles into a target tissue of a vertebrate subject, the method comprising:

providing particles in a needleless syringe; and effecting a controlled release of gas down a duct of the syringe, said gas having a maximum total pressure of about 10 bar or less, whereby to accelerate the particles down the duct to exit the duct with sufficient energy as to penetrate into a target tissue of a vertebrate subject.

BRIEF DESCRIPTION OF THE FIGURES

Six embodiments of needleless syringe device in accordance with the present invention will now be described, by way of example only, with reference to the accompanying schematic drawings in which:

FIG. 8 is an axial section through a sixth embodiment of the needleless syringe device;

FIG. 11 is a perspective view of a payload package for use with the sixth embodiment of the invention;

DETAILED DESCRIPTION

Figure 1:
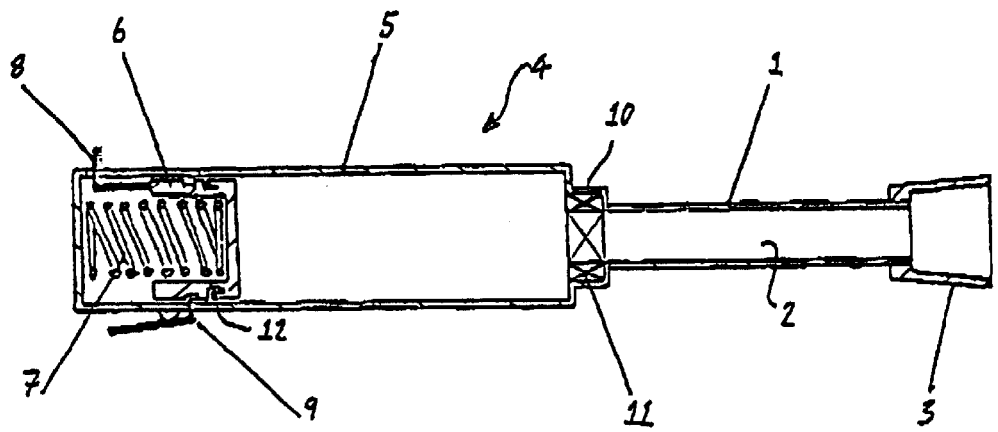
FIG. 1 is an axial section through a first embodiment of the needleless syringe device.

The first embodiment of device is an air-powered, re-usable device.

The device includes an elongate, tubular duct 1 having a lumen 2 for delivering particles towards a target tissue (not shown). The duct has an upstream end and a downstream end. The downstream end of the duct may, as shown, be provided with a divergent spacer 3. In this first embodiment the duct lumen is approximately 6 mm in diameter and is of substantially constant cross-sectional area.

The device further comprises a gas discharge chamber 4. This chamber 4 comprises a cylinder 5, for example of approximately 18 mm internal diameter, with a piston 6 slidably received therein. The piston 6 seals against the barrel of the cylinder 5, due to the presence of a sealing ring 12, and is movable linearly within the cylinder 5 between a first position (shown) and a second position (not shown). To drive the piston 6 along the cylinder 5 from its first position to its second position a spring 7 is provided. To enable the gas discharge chamber 4 to be primed a priming lever 8 is provided to enable the piston 6 to be pulled back, against the biasing force of the spring 7, to its first position. To retain the piston 6 in its first position an actuation trigger 9 is provided. The actuation trigger is shown schematically as being pivotally attached to the exterior wall of the cylinder 5 whereby, on squeezing the left hand end of the trigger 9 upwardly (as drawn), the opposite end of the trigger 9 will be removed from engagement with a recess provided in the skirt of the piston 6, freeing the piston 6 to be driven from its first position to its second position by the compression energy stored in the spring 7. It will be understood that, in moving rapidly from its first position to its second position, the piston 6 will sweep at least part of the internal volume of the cylinder 5 to displace from the cylinder any gas previously contained therein.

It is envisaged that the components making up the gas discharge chamber could be made of metals and/or plastics materials.

In the preferred arrangement illustrated a receptacle 10 is provided between the main body of the duct 1 and the gas discharge chamber 4. This receptacle may, as shown, take the form of a stepped region at the upstream end of the duct 1, or a stepped region at the downstream end of the cylinder 5. Advantageously, the duct 1 and receptacle 10 are formed integrally as a combined duct/receptacle assembly and are detachable from the cylinder 4. In this way, after gas has been discharged from the chamber 4 to accelerate the particles from the receptacle 10 and the duct 1 (as described below), the assembly can be separated from the gas discharge chamber 4 and disposed of. A fresh duct/receptacle assembly, containing a fresh charge of particles, could then be connected to the re-primed gas discharge chamber 4 to enable the device to be reused.

Although in the illustrated embodiment the receptacle 10 is positioned upstream of the upstream end of the duct lumen 2, such that the receptacle 10 and duct 1 are distinct, it is envisaged that the receptacle could be defined, either in part or in totality, by the duct lumen 2. For example, some or all of the duct lumen 2 might be filled with the particles to be delivered.

A drug capsule 11 is shown schematically in the receptacle 10 in FIG. 1. This drug capsule 11 holds the particle or particles to be accelerated by the device into a target tissue, either containing the particle(s) or constituting the particles(s). Usually, a large number of particles will be assembled together to form a capsule. Preferably the capsule 11 does not include a bursting membrane of the sort described in Bellhouse et al. A bursting membrane or membranes may however be used to contain the particles. Alternatively, the particles could be loaded into the receptacle 10 as loose powder, and/or loosely adhered to the annular wall of the receptacle 10.

It will be appreciated that, when the device is primed and the actuation trigger 9 is then operated, the rapid movement of the piston 6 from its first position towards its second position will pressurize the interior of the cylinder 5 to a peak pressure of about 10 bar or less. This controlled discharge of pressurized air will lead to a build up of higher pressure air on the left hand side of the drug capsule 11, which will cause any particle-retaining membrane(s) to burst and the particles held in the drug capsule 11 to be accelerated down the lumen 2 of the duct 1, to be ejected at high velocity from the downstream end of the duct. The maximum particle ejection velocity will be of the order of 50–300 m/s, more preferably 50–150 m/s or 50–100 m/s.

Upon effecting a controlled discharge of pressurized air from the chamber 4, the lumen diameter and pressurised air pressure ensure that the air flow rate cannot exceed the choked mass flow rate of the duct lumen for any sustained period of time. The absence of a convergent-divergent duct means that the air flowing through the duct lumen 2 is not accelerated to the same extent as the air that travels through the convergent-divergent duct in the Bellhouse et al device. Despite this, it has been found that the particles of the appropriate size and density can be accelerated down the duct lumen 2 to exit the duct 1 with sufficient energy as to enable them to penetrate into a target tissue of a vertebrate subject to a desired depth, for example between 10 and 500 µm.

The preferred construction for the duct lumen is cylindrical, or nearly cylindrical. The duct may advantageously be moulded from plastics material and, for reasons of ease of production, it is usually necessary to employ a slight taper. The preferred construction of the duct lumen differs from that of the nozzle lumen disclosed in Bellhouse et al., in that the duct lumen illustrated in FIG. 1 does not converge and then diverge to form a throat.

In the nozzle lumen disclosed in Bellhouse et al., the convergence ensures that the steady state gas flow in the throat is choked to have a velocity of Mach 1 at the throat of minimum section. The velocity in the throat cannot exceed Mach 1. The divergence downstream of the throat expands the gas to supersonic speed.

"Steady state" means the condition in which the gas flow velocities (at any point in the duct) change relatively slowly with time. Also, any shock waves formed tend to be stationary or slowly moving.

It will be appreciated that the duct lumen of the device of the present invention could have a divergent section. Even though the duct, lumen shape influences the flow velocity, what is important is that the gas flowing through the duct lumen cannot expand to achieve a steady state supersonic velocity, rather than the particular duct lumen design which is employed to achieve this result.

Relative to the supersonic needleless syringe described in Bellhouse et al., the first embodiment of needleless syringe device illustrated in FIG. 1 has the ability to be made and operated more cheaply. Unlike some supersonic devices which require one-shot helium canisters, the device is air-powered and does not require a self-contained capsule of pressurized gas. Instead, the air power is derived by use of a spring-loaded piston and cylinder arrangement that can be reused many times. Furthermore, it is thought that the device does not require the particles to be contained between burstable membranes. In addition, the fact that the air flow does not reach supersonic velocity in the steady state means that the device is more energy efficient and that less gas is required than with a supersonic needleless syringe, enabling the device to be made smaller and to be used more discretely. Furthermore, because the shock waves associated with a supersonic flowfield are not present, the "sonic boom" which is audible upon operation of a supersonic device does not occur, reducing or removing the need for a silencer. Despite the absence of very high speed gas flow conditions in the duct lumen, the particles have been found to be accelerated sufficiently within the duct lumen to exit it with sufficient energy to penetrate into target tissue to the required depth, such as 10–500 µm.

EXAMPLE 1

The purpose of this example is to describe, in non-limiting fashion, the use of the embodiment of the needleless syringe device illustrated in FIG. 1 to deliver lidocaine (a local anaesthetic) to the back of the hand and the anticubital fossa.

I. Method

The right or left arm of each volunteer was selected at random and the volunteer was asked to look away from the direction of the selected arm. The back of the hand and anticubital fossa were pricked with a 22 gauge hypodermic needle, considered by the investigator to be commensurate with a puncture required for venous cannulation. The volunteers were then asked to rate the pain they felt on a scale of 1–10, 1 being no pain and 10 being the most pain imaginable from a needle stick. The device was then fired and the volunteers were asked to rate the pain they felt as it changed over time.

II. Results

With no treatment, the mean pain for the back of the hand score was 8 and the anticubital fossa 9. One minute after actuation of the device, clear erythema could be seen approximately 10 mm in diameter. Powder, presumably lidocaine, could be seen clearly on the surface of the skin which served -to show where the device had been shot. In no instances was any damage or bleeding observed caused by the actuation of the device. The actuation of the device was not considered painful by any of the volunteers, nor the noise considered too loud.

Figure 2:
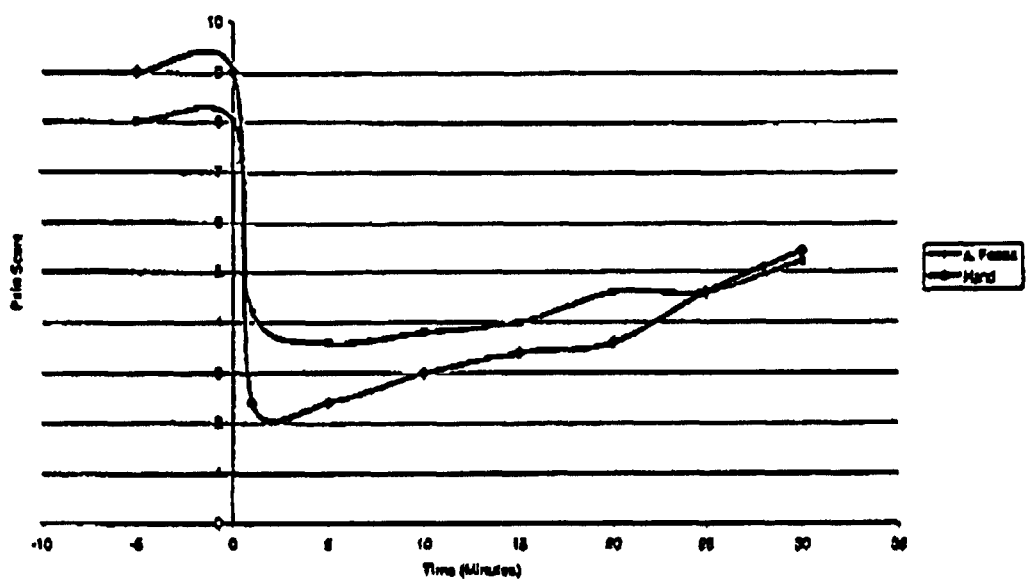
FIG. 2 is a plot of pain score against time following lidocaine administration using the first embodiment of device.
Figure 4:
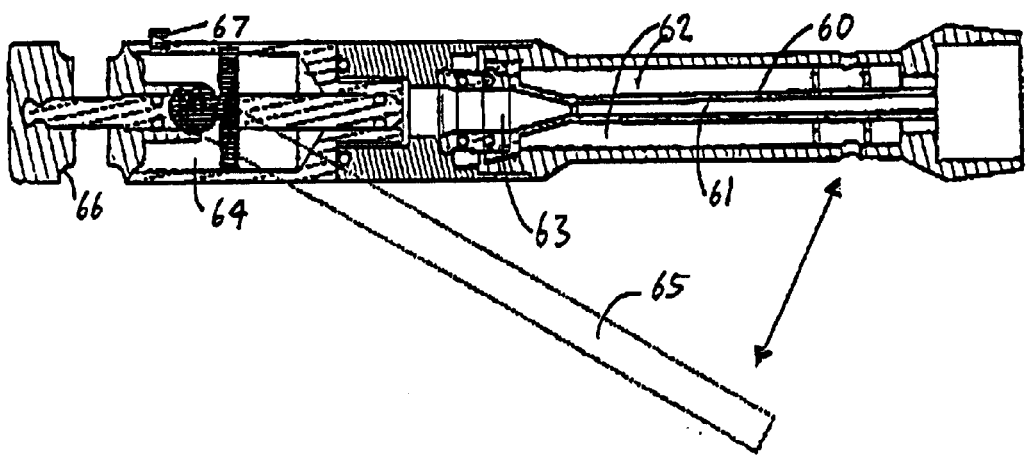
FIG. 4 is an axial section through a third embodiment of the needleless syringe device.
Figure 5:
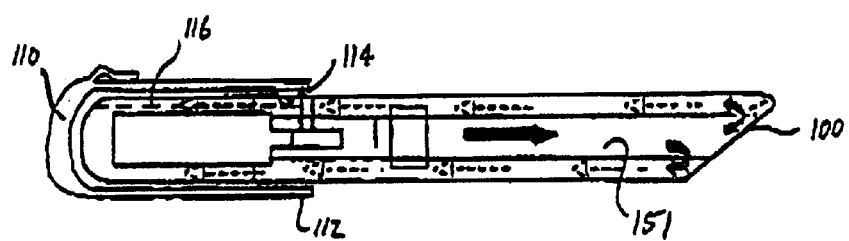
FIG. 5 is an axial section through a fourth embodiment of the needleless syringe device.
Figure 6:
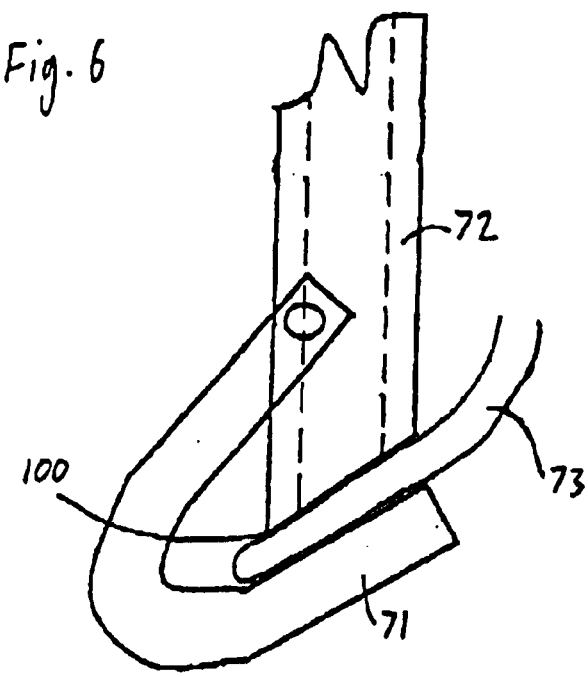
FIG. 6 is a close up of the exit of the device shown in FIG. 5.
Figure 7:
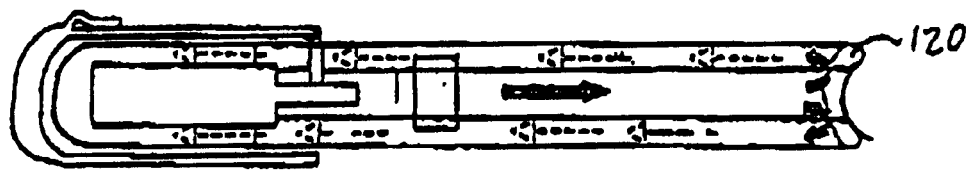
FIG. 7 is an axial section through a fifth embodiment of the needleless syringe device.
Figure 9:
FIG. 9 is a perspective view of a double-sided corrugated sheet used in the sixth embodiment of the invention.
Figure 10:
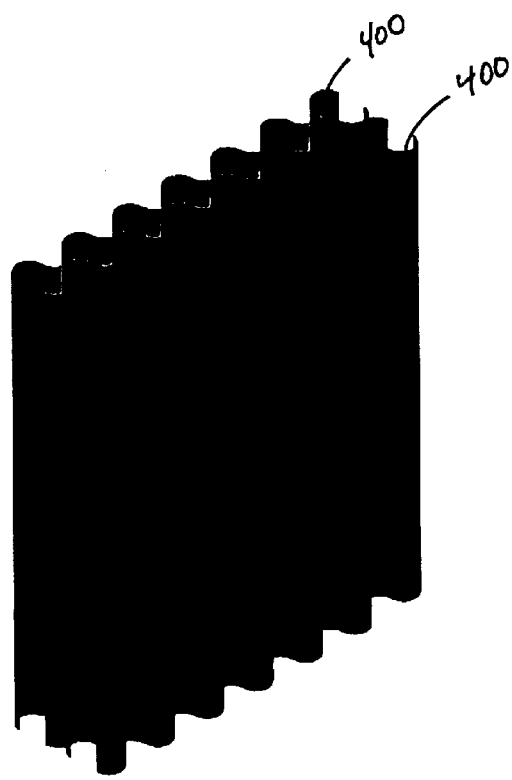
FIG. 10 is a perspective view of a plurality of the sheets shown in FIG. 9 adhered together.
Figure 12:
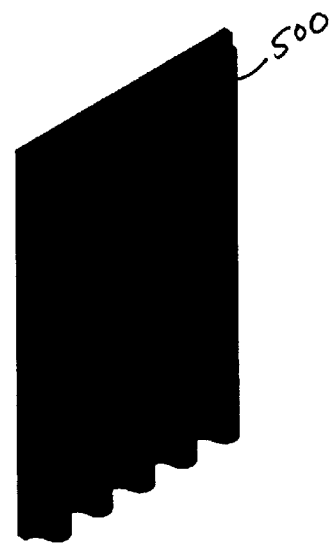
FIG. 12 is a perspective view of a single sided corrugated sheet being an alternative sheet for use in the syringe device of FIG. 8.
Figure 13:
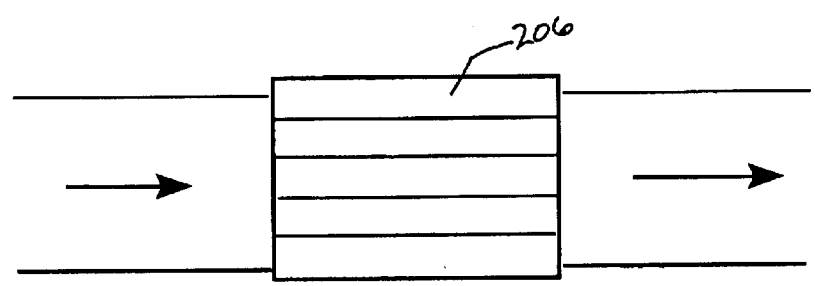
FIG. 13 shows a method for filling a payload package according to the sixth or seventh embodiments of the invention.

Topical anaesthesia was observed after 1 minute, which increased at the five-minute time point and then fell away gradually over the next 25 minutes. FIG. 2 is a plot of pain score, versus time (minutes) following lidocaine administration, in Example 1. The anaesthesia at the anticubital fossa was greater than the back of the hand.

Although the above test was performed with lidocaine, it is considered that the needleless syringe device of the present invention is suitable for the transdermal delivery of multiple different therapeutic agents, for delivery of genetic material into living cells (e.g. gene therapy) and for the delivery of biopharmaceuticals to skin, muscle, blood or lymph. The needleless syringe of the present invention can further be used for the delivery of diagnostic products, for example, substantially inert particles for use in diagnostic sampling of analytes and fluids. It is, thus, envisaged that the device can be used to deliver a very wide range of therapeutic agents that can be delivered topically or systemically.

Accordingly, in one embodiment, the needleless syringe of the present invention is loaded with particles of a therapeutic agent and used to deliver a drug, vaccine or other compound or composition in the context of a therapeutic or prophylactic method. In another embodiment, the needleless syringe is used to deliver diagnostic particles, for example in the context of a diagnostic sampling for an analyte of interest.

As used herein, the terms "therapeutic agent" and/or "particles of a therapeutic agent" intend any compound or composition of matter which, when administered to an organism (human or animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, horm ones, biological response modifiers, nucleic acids, gene constructs and the like. More particularly, the term "therapeutic agent" includes compounds or compositions for use in all of the major therapeutic areas including, but not limited to, adjuvants, anti-infectives such as antibiotics and antiviral agents; analgesics and analgesic combinations; local and general anesthetics; anorexics; antiarthritics; antiasthmatic agents; anticonvulsants; antidepressants; antigens, antihistamines; antiinflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both doubleand single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol; dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

The term "analyte" is used herein in its broadest sense to denote any specific substance or component that one desires to detect and/or measure in a physical, chemical, biochemical, electrochemical, photochemical, spectrophotometric, polarimetric, colorimetric, or radiometric analysis. A detectable signal can be obtained, either directly or indirectly, from such a material. In some applications, the analyte is a physiological analyte of interest (e.g., a physiologically active material), for example glucose, or a chemical that has a physiological action, for example a drug or pharmacological agent.

As used herein, the term "sampling" means extraction of a substance from any biological system across a membrane, generally across skin or tissue. The membrane can be natural or artificial, and is generally animal in nature, such as natural or artificial skin, blood vessel tissue, intestinal tissue, and the like. A "biological system" thus includes both living and artificially maintained systems.

To enable easy refilling of the receptacle 10 with a fresh charge of particles after the device has been operated to expel a first charge of particles, the receptacle 10 may be provided with an openable and closable door (not shown). In this case the duct 1 would not need to be separated from the gas discharge chamber 4 to effect refilling.

In the illustrated embodiment the cylinder 5 is approximately 80 mm long and the combined length of the duct 1 and spacer 3 is approximately 60 mm. It is considered that the longer the length of the duct 1, the higher the exit velocity of the particles is likely to be due to the particles having a greater chance to reach gas velocity.

It is considered that the first embodiment of needleless syringe device may well be able to achieve good particle-skin penetration performance by discharging less than 4 ml of gas, preferably less than 2 ml of gas, at a peak pressure of about 10 bar or less.

Although in FIG. 1 the bore of the cylinder 5 is greater than the lumen 2 of the duct, this need not be so. The diameters upstream and downstream of the receptacle 10 could be the same. Consequently, the main structure of the device could essentially be a tube of constant diameter from one end to the other, with the piston running in a cylinder having a bore equal to the duct lumen's diameter.

Though it is conceived that the first embodiment of needleless syringe device will, most usually, be used to deliver a large number of particles, it is envisaged that the device will be capable of discharging small numbers of particles, even just a single, relatively large particle, for example a particle of several hundreds of microns. It is thought that the device of the present invention will exercise a degree of self-regulation, in that the bigger the size of particle or particles that is discharged the lower will be the particle(s) discharge velocity. Thus, the momentum of each of the particles is expected to be broadly similar. Furthermore, due to the maximum gas velocity being lower in the device of the present invention, relative to a supersonic device of the sort described in Bellhouse et al., problems associated with large particles travelling too fast can generally be avoided.

An advantage of using the first embodiment's preferred piston/cylinder arrangement for the gas discharge chamber is that, relative to using a single-shot sealed gas canister, one will obtain a relatively lengthy period of generally constant flow conditions in the duct lumen 2. This is because the spring continuously pressurises the gas as it moves along the cylinder. In contrast, with a one-shot canister after the attainment of the maximum initial pressure the gas pressure falls exponentially. It is thought that the illustrated piston/cylinder arrangement thus makes the device very efficient in terms of being able to achieve good particle exit velocities despite a low gas volume and pressure.

Figure 3:
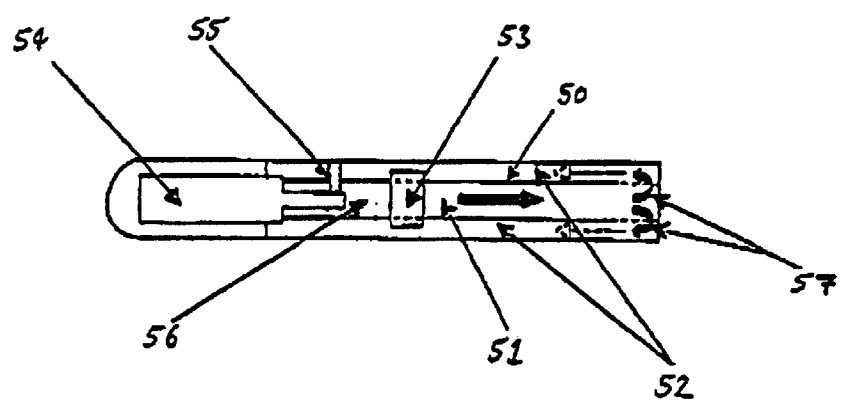
FIG. 3 is an axial section through a second embodiment of the needleless syringe device.

FIG. 3 illustrates (schematically) a second embodiment of needleless syringe device in accordance with the present invention. In common with the first embodiment, the second embodiment includes an elongate, tubular duct 50 having a lumen 51 for delivering particles towards a target tissue (not shown). Preferably the duct lumen 51, as illustrated, has a substantially constant diameter along its length.

In the region of the upstream end of the duct 50 there is provided a chamber 52. In the illustrated embodiment this contains a very low cracking pressure payload package 53 with the same, or nearly the same, cross-sectional flow area as that of the duct lumen 51. The exterior of the duct 50 is provided with an exhaust chamber 52, with the arrows 57 denoting reverse gas flow into the exhaust chamber.

One main difference between the needleless syringe devices of the first and second embodiments is in the form of the gas discharge chamber. In the second embodiment the gas discharge chamber takes the form of a canister 54 pre-charged with gas, such as $CO_2$, N, He or air. Advantageously, the canister 54 is removable from the device and replaceable so as either to enable the removed canister to be refilled or to enable a fresh, non-reusable canister to be fitted, so as to reprime the device.

The device may be provided with a metering system to enable a single gas canister to be successively, partly discharged, enabling multiple "shots" to be obtained from a single canister 54. Alternatively, a gas canister may just provide a single "shot". To enable release of gas from the canister an actuation pin 55 is shown schematically.

An advantage of having the gas canister 54 face in the downstream flow direction is that it enables the use of an expansion chamber 56 of smfall volume.

In common with the first embodiment, the second embodiment of the needleless syringe device is designed such that compressed gas will not expand in the duct lumen 51 to the very high speeds disclosed in Bellhouse et al. The main feature that ensures that the flow within the duct lumen 51 does not become very fast is selecting a compressed gas pressure of about 10 bar or less so that the average gas mass flow rate falls below the choked mass flow rate for the nearly constant-area duct lumen 51. Another feature that contributes to the absence of very high speed gas flow is the absence of a convergent-divergent nozzle. This has further advantages in that a constriction, which tends to concentrate the particles to the centre of the jet, is not present.

Preferably, the particles to be delivered take the form of a package that avoids the need for a bursting membrane or a high cracking pressure non-membrane package. This has the effect of allowing a reduced driver pressure to be used in the expansion chamber 56, which prevents choked flow conditions from prevailing in the duct lumen 51. It is also thought that the elimination of a bursting membrane, or a high cracking pressure particle package, prevents the generation of a high pressure ratio across the particle package, which eliminates the creation of a strong moving normal shock wave that might then propagate through the duct lumen.

Ideally, the choked mass flow rate of the gas canister 54 is matched to the required mass flow rate in the duct lumen 51 to achieve steady state gas velocities in the duct lumen 51 that are well subsonic, for example 200 m/s when using air.

By reducing the mass flow requirements of the duct lumen 51, the pressure-volume requirements of the gas canister 54 may advantageously be reduced. This reduced mass flow rate reduces silencing requirements. Operating at average speeds that are not supersonic further reduces acoustic noise associated with the existence of shock waves in a flow field. This is expected to reduce silencing requirements, resulting in a compact device size and/or allowing the delivery of higher payloads than a comparable supersonic needleless syringe device.

FIG. 4 illustrates (schematically) a third embodiment of a needleless syringe device in accordance with the present invention. In common with the first two embodiments, a tubular duct 60 having a lumen 61 for delivering particles towards the target tissue (not shown) is included. Preferably the duct lumen 61 has a constant diameter along its length, or diverges only very slightly (as shown). This embodiment differs from the first and second embodiments mainly by virtue of its gas discharge chamber 64. In the third embodiment, a hand lever 65 may be repeatedly pumped in order to build up pressure in chamber 64. Pressures of between 5 and 10 bar may be achieved in chamber 64 by using the hand lever. The device is actuated by pressing the button 66 which releases the gas from the chamber 64 so that it may travel down the lumen 61. A payload package 63 is designed to crack under a very low pressure so that the pressure which the hand lever is capable of producing in the chamber 64 is sufficient to crack the payload package. A gas valve 67 (set at 10 bar) may be provided in the wall of chamber 64 so as to release additional gas to avoid over pressurisation.

A fourth embodiment of the invention is shown schematically in FIG. 5. This embodiment is very similar in form and function to the second embodiment shown in FIG. 3, but as may be seen, the exit plane 100 is not perpendicular to the longitudinal axis of the nozzle, but is angled relative to the axis.

Previous devices have had exit planes that are essentially normal to the longitudinal axis of the nozzle which can make it difficult to use in confined body areas such as in the mouth. This has led to sealing problems which can result in the particles exiting the device upon actuation without penetrating the target. The fourth embodiment has an exit plane 100 that is oriented at an angle to the longitudinal axis of the duct 151. This makes it easier to hold the angled end face of the device against the target tissue to maintain a more effective seal. This seal may further be improved by using a soft elastomeric sealing material at the exit plane of the device. This sealing material may, however, be rigid if the tissue to which it is intended to be sealed is flexible.

Also shown in FIG. 5 is a cap 110 which is intended to fit over the upstream end of the device in the same way that a pen cap fits over a pen. It is envisaged that this cap will initially be positioned over the downstream end of the device and as such, will protect the duct from contamination during shipping and handling. The pocket clip 112 on the cap will also allow easy transportation in a shirt/coat pocket.

When it is intended to use the device, the cap 110 is removed from the downstream end and placed on the upstream end of the device. In a preferred arrangement the end cap is provided with an inwardly protruding feature 114 that can be received in a groove or grooves 116 in the outside of the device at its upstream end. This inwardly protruding feature 114 could serve to trigger actuation of the device so that actuation is impossible unless the cap 110 has been removed from the downstream end and placed correctly onto the upstream end. The inwardly protruding feature 114 could have a ramp profile so as to depress the actuation pin and fire the delivery system. Normally, the actuation pin would sit in the groove 116 and thus be located below the outside surface of the device to prevent inadvertent actuation of the device.

Although in FIG. 5 above, the cap 110 and angled end section 100 are described together, this is only for the sake of conciseness and in practice one could be used without the other. For example, the end cap could be used in devices which do not have angled exit planes. FIG. 6 shows a close up of the exit plane 100 of the device in FIG. 5 with the additional feature of a positioning bracket 71. The positioning bracket 71 is attached to the outside wall 72 in a pivotable fashion. The bracket is particularly intended for use in the mouth and would initially be pivoted back from the position shown so as to allow easy insertion into the mouth. Once the angled exit plane has been aligned to be parallel to the target mucosal tissue 73, the bracket may then be swung forward such that it is nearly parallel to the exit plane of the device in the manner shown in FIG. 6. In this position, the bracket can support the tissue 73 into which delivery will occur to increase the effectiveness of the device-to-tissue seal.

FIG. 7 shows a fifth embodiment of a needleless syringe device according to the present invention. This embodiment is substantially the same as the fourth embodiment with the difference that the angled exit plane 100 has been replaced by a generally concave exit plane 120. The exit plane may also have an elastomeric seal to aid in sealing. This embodiment is particularly useful for the treatment of MED (Mail Erectile Disfunction). The concave shape of the exit plane 120 is ideal for use in the delivery of alprostadil or other drugs directly to the glans of the penis.

FIG. 8 shows a sixth embodiment of the invention. As can be seen in FIG. 8, the needleless syringe of the sixth embodiment comprises a gas reservoir 200 having a plunger 202. When the plunger 202 is depressed, the O-ring 210 moves outwardly from the reservoir allowing gas to escape in the downstream longitudinal direction. The gas first encounters a filter 204 which is positioned between the end of a slightly divergent tapered section and the beginning of a constant cross-sectional lumen. The filter serves to remove any particulate matter entrained in the gas coming from the reservoir 200. Immediately downstream of the filter 204 is the payload package 206. This package comprises a plurality of tubeways, each or some of the tubeways having particles adhered to their inner surfaces. After the payload package 206, the duct lumen 208 extends downstream with a constant cross-section.

The reservoir 200 is initially filled with gas (e.g. helium or air) having a pressure of about 10 bar or less. The total pressure of the whole system is therefore also less than 10 bar at any time during the operation of the device.

After actuation, gas flows out of the reservoir 200 and is choked by the constriction formed by the reservoir valve. This fixes the maximum mass flow rate through the device. As the gas flows through the reservoir valve, it spreads out to occupy substantially the entire width of the device. The gas then flows through the filter 204 and into each of the plurality of tubeways. The gas passes through the tubeways and out of the device via the constant cross-section duct. The particles initially adhered in the tubeways of the payload package 206 are stripped from the sides of tubeways when the velocity of the gas therethrough reaches a critical magnitude. The particles are then entrained in the gas flow and flow downstream out of the device.

The tubeways of the payload package 206 are substantially uniformly distributed over the entire cross-section of the duct 208. Furthermore, the particles to be accelerated are substantially uniformly distributed over the inner surfaces of the tubeways.

This "honeycomb" composition of the payload package 206 provides three main advantages. The first is that the payload of particles is initially even distributed across the whole cross-section of the device at the time when the particles are entrained. This uniform distribution at entrainment helps lead to a more uniform distribution of particles as they leave the device and enter the target tissue. The construction of the payload package therefore provides a more even exit distribution of particles than when the particles are simply retained between two burstable membranes or when they are adhered to the inside of the lumen duct.

The second advantage is that no burstable membranes are required. Thus, there is no sudden step change in pressure produced by the bursting of a membrane. Instead, the particles are released into the flow when the velocity of gas through the payload package is sufficient to detach the particles from the inner walls of the tubeways.

Thirdly, the payload package of the sixth embodiment makes it easy and convenient to adjust the amounts of particles in the package by simply adjusting the length of the payload package 206. This can be done by trimming the package with scissors or another sharp implement. This is due to the fact that the particles are evenly distributed in the longitudinal direction in each of the tubes, as well as in the circumferential direction.

FIG. 9 shows a double-sided corrugated thermofonied sheet 400 suitable for use in the manufacture of the payload package 206. The sheet may be made from any suitable polymer and may be created using a thermoforming process. The polymer itself may be sticky, in which case the sheet does not need to be treated, or the polymer could be non-sticky, in which case the sheet can be covered on one or both sides with an adhesive. Several of the sheets 400 shown in FIG. 9 are stacked together to provide parallel rows of tubeways as shown in FIG. 10. The plurality of corrugated sheets may be joined together using any appropriate means, e.g. mechanically, an adhesive, a laser weld, etc.

Alternatively, the stacked sheets could be temporarily held together, cut into the final package dimensions and pushed into or held in place within an outer package. This configuration is shown in FIG. 11. To prevent sliding of the individual sheets, they may be tacked to each other after they are inserted into the outer package 300, or a retaining ring 302 may be provided on the package or the syringe itself to retain them in place.

As an alternative to the double sided corrugated sheets 400 shown in FIG. 9, a single sided corrugated injection moulded sheet 500 may be used as shown in FIG. 12.

In the case where sticky polymers are used to make the corrugated sheets or the sheets are sprayed with adhesive prior to assembly of the payload package, the particles may be applied to the inner surfaces of the tubeways after the payload package has been assembled. A method for doing this is shown in FIG. 13. As can be seen in this Figure, a fluidized flow of particles is established so as to be aligned with the longitudinal direction of the tubeway. As the particles flow through the sticky tubeways, they adhere to the side. After a certain time period, the particles are found to be evenly distributed within the tubeways, both longitudinally and circumferentially. After loading with particles in this way, a plurality of payload packages can be cut from the single package that has been exposed to the flow of fluidized particles. The dose can be determined by appropriate choice of the length of package.

For the case when a non-sticky polymer is used, the corrugated sheets may be loaded with particles using spray-coating techniques before being assembled into a payload package.

The cross-sectional area of each tubeway in the package is preferably designed to ensure that a critical local flow velocity that effectively strips and entrains the payload is provided during the operation of the device. The payload package is preferably also designed to have no crevices which create stagnation points in the flow.

In a further embodiment (not illustrated), the corrugated sheets can be rolled into a circular tube to provide a payload package that looks like a pleated filter element. The rolled shape can either be tacked together to form a self-contained payload package, or it can be pushed or inserted into a larger diameter hollow tube section to create a stand alone payload package.

The sixth embodiment of the invention improves the even distribution of the payload prior to entrainment and thereby improves the even distribution of the payload across the target diameter. No rupturable membranes are required (although they could be used, if desired), which can eliminate the complex flows that can be associated with the rupturing of a membrane having a pressure differential across it. Also, the payload package design eliminates membrane fragments that may be entrained in the gas flow when rupturable membranes are used.

The fact that the particles are evenly distributed across the cross-section of the duct improves particle entrainment reproducibility from shot to shot and thereby reduces shot-to-shot performance variability. Further, the fact that the payload is evenly distributed also increases the total amount of payload that can be delivered since there are no portions of the flow having a high payload density compared to other portions, the maximum payload density determining the maximum payload.

In all of the above embodiments, vanes and/or rifling may be used near the exit plane of the devices to help spread the payload. These vanes could protrude from the inside walls of the duct into the gas flow stream and run the entire length of the acceleration duct in a helical fashion so as to impart a rotational spin on the gas and particle flows. The curvature of the vanes should be of an angle appropriate to achieve the required payload particle characteristics and distribution. Alternatively, the vanes could be confined to just the downstream exit section.

An advantage thought to be common to each of the above described embodiments of devices is one of engineering development. Through avoiding very high gas speeds in the duct lumen, it is considered that it will be comparatively easy to modify the skin impact velocity of particles for clinical end point or dermal tolerability considerations.

The previously proposed technique of Bellhouse et al, of using a converging-diverging nozzle in supersonic needleless syringe devices to accelerate compressed gas to supersonic speed, forces the gas and particles to flow through a constriction in the nozzle lumen, namely through a throat area. If a nozzle lumen is to steadily expand compressed gas to supersonic speed it must first cause choked flow (usually achieved by convergence) and then diverge. It must, therefore, have a throat area that is defined as the section of the duct which has a minimum cross-section area.

The need for a minimum cross-sectional area throat in steady flow supersonic devices poses a significant problem in designing a compact needleless syringe device because the throat provides a constriction in the nozzle lumen. It is thought that this constriction impedes efficient particle acceleration because of the high solids-to-gas ratio in the flow. It is further thought that the throat constriction also results in large acceleration gradients in the gas flow that can cause shear stresses on the particles passing therethrough, leading to significant particle-gas attrition (i.e. particle break-up due to bombardment by gas molecules). The throat constriction in steady flow supersonic needleless syringe devices also forces the particles closer together as they traverse the throat section under very high acceleration forces. It is thought that this can lead to undesirable particle-particle shear forces, resulting in particle-particle attrition (i.e. particle break-up due to particles colliding with one another). Forcing particles that are accelerating at high speed through a minimum-area throat constriction of a supersonic device can also lead to significant particle-lumen attrition (i.e. particle break-up due to particles hitting the lumen wall). By eliminating the throat area in the preferred, illustrated forms of duct lumen, it is expected that there will be benefits in reducing particle-gas, particle-particle and particle-lumen attrition. This may improve delivery of fragile payloads and/or offer the possibility of delivering higher payloads.

A further possible advantage of operating at lower gas flow velocities than in Bellhouse et al may come around in improving the ease of modifying the particle-skin impact velocity. It is thought that it will be possible to change this velocity by changing the ratio of the gas mass flow rate in the duct lumen to the choked mass flow rate from the gas source (by adjusting the cross-sectional area of the duct lumen), or by reducing the choked mass flow of the gas source for a given substantially constant cross-sectional area duct lumen (by reducing the area of the gas source opening). It is envisaged that this may provide improved flexibility in configuring a needleless syringe design for a given application.

What is claimed is:

1. A needless syringe device for accelerating particles into a target tissue of a vertebrate subject, said syringe comprising:
   an elongate, tubular duct having a lumen for delivering the particels towards the target tissue, the duct having an upstream end and a downstream end;
   a receptacle holding the particles to be accelerated; and
   a gas discharge chamber, upstream of the receptacle for the controlled discharge therefrom of pressurized gas to accelerate the particles from the receptacle down the duct lumen towards the target tissue;
   wherein the pressurized gas discharged from the gas discharge chamber has a maximum total pressure, which is less than 10 bar, and which is sufficient to accelerate the particles down the duct such that the particles are configured to exit the duct with sufficient energy to penetrate into the target tissue.

2. A device as claimed in claim 1, wherein the receptacle does not contain a membrane or membranes which burst(s) upon said controlled gas discharge.

3. A device as claimed in claim 1, wherein the particles have a size and density such that, upon effecting a said controlled gas discharge, the majority of the particles will penetrate into the target tissue to a depth of between 10 and 500 μm.

4. A device as claimed in claim 1, wherein the device is arranged so that, upon effecting a said controlled gas discharge, the pressurized gas mass flow rate in the lumen is not greater than the choked mass flow rate of the duct lumen.

5. A device as claimed in claim 1, wherein the gas discharge chamber comprises a cylinder containing a piston movable therein between first and second positions, wherein to effect a said controlled gas discharge the piston is driven along the cylinder from its first position to its second position.

6. A device as claimed in claim 5, wherein the gas discharge chamber further comprises a spring to drive the piston along the cylinder from its first position to its second position.

7. A device as claimed in claim 6, wherein the gas discharge chamber further comprises a priming arrangement to enable the piston to be drawn back from its second position to its first position to compress the spring and thus to prime the gas discharge chamber.

8. A device as claimed in claim 7, wherein the gas discharge chamber further comprises an actuation trigger for releasing the piston from its first position once the gas discharge chamber is primed.

9. A device as claimed in claim 6, wherein the gas discharge chamber is arranged to deliver pressurized gas at a substantially constant pressure for the majority of the travel of the piston from its first position to its second position.

10. A device as claimed in claim 1, wherein the gas discharge chamber comprises a canister pre-charged with gas.

11. A device as claimed in claim 10, wherein the gas is $CO_2$.

12. A device as claimed in claim 10, wherein the gas is He.

13. A device as claimed in claim 10, wherein the gas is air.

14. A device as claimed in claim 10, wherein the gas canister is removable from the device and replaceable.

15. A device as claimed in claim 1, wherein the duct lumen does not contain any constrictions.

16. A device as claimed in claim 10, wherein the gas canister is arranged to be only partly discharged upon effecting a single said controlled gas discharge.

17. A device as claimed in claim 1, wherein the duct lumen does not converge and then diverge.

18. A device as claimed in claim 1, wherein the duct lumen does not substantially diverge in the downstream direction.

19. A device as claimed in claim 18, wherein the downstream end of the duct is provided distally thereof with a divergent spacer.

20. A device as claimed in claim 1, wherein the duct lumen does not substantially converge in the downstream direction.

21. A device as claimed in claim 1, wherein the duct lumen is of substantially constant diameter along its length.

22. A device as claimed in claim 1, wherein the device is of modular construction and the duct and gas discharge chamber may be separated to allow the filling of the receptacle with particles to be accelerated.

23. A device as claimed in claim 1, wherein the receptacle containing the particles to be accelerated takes the form of a self-contained capsule.

24. A device as claimed in claim 23, wherein the capsule does not include a membrane that is required to be burst to release the particles upon effecting a said controlled gas discharge.

25. A device as claimed in claim 1, wherein the receptacle is defined, at least in part, by the duct lumen.

26. A device as claimed in claim 1, wherein the receptacle is positioned upstream of the upstream end of the duct lumen.

27. A device as claimed in claim 1, wherein the device is arranged to accelerate the particles to a maximum velocity in the range of about 50–300 m/s upon effecting a said controlled gas discharge.

28. A device as claimed in claim 27, wherein the device is arranged to accelerate the particles to a maximum velocity of the order of 50–150 m/s.

29. A device as claimed in claim 28, wherein the device is arranged to accelerate the particles to a maximum velocity of the order of 50–100 m/s.

30. A device as claimed in claim 1, wherein the gas discharge chamber is arranged to discharge less than 4 ml of gas.

31. A device as claimed in claim 30, wherein the gas discharge chamber is arranged to discharge less than 2 ml of gas.

32. A device as claimed in claim 1, wherein the receptacle has a cross-sectional area generally similar to that of the immediately adjacent downstream portion of the duct lumen.

33. A device as claimed in claim 1, further comprising at least one burstable membrane which bursts upon said controlled gas discharge.

34. A device as claimed in claim 33, wherein said burstable membrane is constructed so as to burst when a pressure difference of a 8 bar is placed across its surfaces.

35. A device as claimed in claim 33, wherein said burstable membrane is constructed so as to burst when a pressure difference of a 6 bar is placed across its surfaces.

36. A device as claimed in claim 1, wherein said receptacle comprises a plurality of tubeways longitudinally aligned with the tubular duct, at least some of the tubeways having particles adhered to their inner surfaces.

37. A device as claimed in claim 36, wherein said plurality of tubeways are formed from a plurality of corrugated sheets adhered together to form a structure having a generally honeycomb construction.

38. A device as claimed in claim 37, wherein said corrugated sheets are loaded with particles prior to being adhered together to form said plurality of tubeways.

39. A device as claimed in claim 37, wherein said corrugated sheets are loaded with particles after being adhered together to form said plurality of tubeways.

40. A device as claimed in claim 39, wherein said corrugated sheets forming said plurality of tubeways are loaded with particles by being longitudinally aligned with a flow of particles such that said particles pass through said tubeways and adhere to an inner side thereof.

41. A disposable duct/receptacle assembly for use in the device claimed in claim 1, wherein the assembly comprises a said duct integral with a said particle-containing receptacle and the assembly is disconnectable from the gas discharge chamber whereby, after a said controlled gas discharge has been effected to accelerate the particles from the receptacle and the duct, the assembly can be separated from the gas discharge chamber and replaced in the device with a fresh disposable assembly.

42. A method of discharging particles from a needless syringe suitable for accelerating the particles into a target tissue of a vertebrate subject, the method comprising:

providing particles in a needless syringe; and effecting a controlled release of gas down a duct of the synringe, said gas having a maximum total pressure of less than 10 bar, whereby to accelerate the particles down the duct to exit the duct with sufficent energy as to penetrate into a target tissue of a vertebrate subject.

43. A method as claimed in claim 42, wherein the particles are discharged into a target tissue of a vertebrate subject.

* * * * *